United States Patent [19]

Lennard et al.

[11] Patent Number: 4,911,165
[45] Date of Patent: Mar. 27, 1990

[54] PLIABILIZED POLYPROPYLENE SURGICAL FILAMENTS

[75] Inventors: David J. Lennard; Edgar V. Menezes, both of Somerville; Robert Lilenfeld, Hopewell, all of N.J.

[73] Assignee: Ethicon, Inc., Somerville, N.J.

[21] Appl. No.: 285,317

[22] Filed: Dec. 12, 1988

Related U.S. Application Data

[63] Continuation of Ser. No. 554,347, Nov. 25, 1983, abandoned, which is a continuation-in-part of Ser. No. 457,350, Jan. 12, 1983, abandoned.

[51] Int. Cl.⁴ .............................................. A61L 17/00
[52] U.S. Cl. ................................ 606/231; 264/210.8; 264/235.6; 264/342 R
[58] Field of Search ..................... 128/335.5; 428/375, 428/421; 264/210.7, 210.8, 235.6, 342 R

[56] References Cited

U.S. PATENT DOCUMENTS 3,048,467 8/1962 Roberts et al. ............................ 18/54
3,106,442 10/1963 Compostella et al. ........... 264/235.6
3,152,380 10/1964 Martin ..................................... 28/72
3,161,709 12/1964 Noether et al. ...................... 264/210
3,359,983 12/1967 Northey et al. ..................... 128/335.5
3,413,397 11/1968 Bierbaum et al. ................... 264/290
3,630,205 12/1971 Listner .

FOREIGN PATENT DOCUMENTS 1588031 7/1977 United Kingdom .

OTHER PUBLICATIONS

Japanese Patent Application No. 66-21576 published 12/16/66.
Japanese Patent Application No. 66-7891 published 4/26/66.

Primary Examiner—C. Fred Rosenbaum
Assistant Examiner—Sharon Rose

[57] ABSTRACT

Polypropylene surgical monofilaments sutures of improved compliance are made by drawing polypropylene monofilament to a greater extent than its natural draw ratio, followed by annealing with shrinkage.

10 Claims, 1 Drawing Sheet

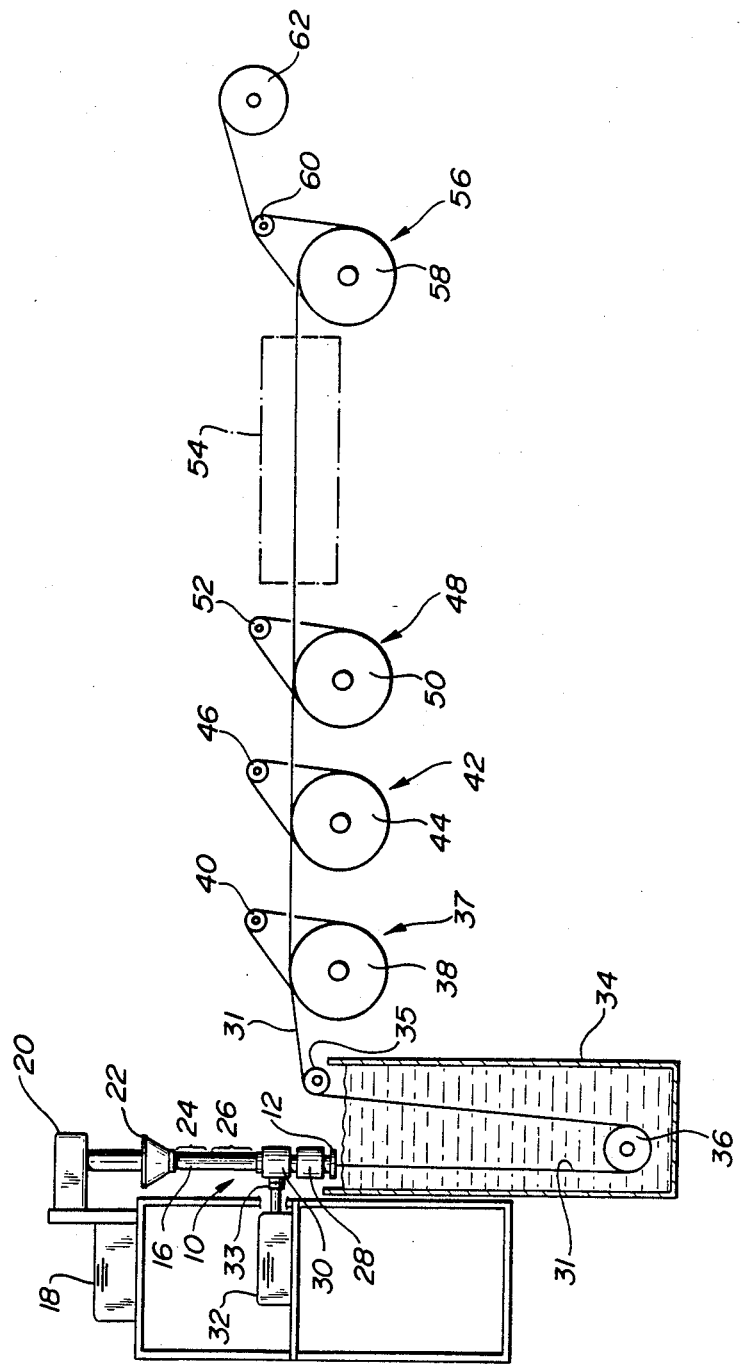

PLIABILIZED POLYPROPYLENE SURGICAL FILAMENTS

This is a continuation of application Ser. No. 554,347, filed Nov. 25, 1983, now abandoned, which is a continuation-in-part of application Ser. No. 457,350, filed Jan. 12, 1983, now abandoned.

The invention relates to polypropylene surgical monofilaments having improved compliance and to a process for making them.

BACKGROUND OF THE INVENTION

Surgical sutures made from polypropylene monofilaments have been successfully used by the medical profession for more than ten years. The advantages exhibited by polypropylene sutures include the following:

(a) They pass easily through tissue;
(b) They resist breakdown and do not promote infection;
(c) They have minimal reaction with tissue;
(d) They have high tensile strength; and
(e) They maintain their in vivo tensile strength over extended periods.

The preferred polypropylene suture used in the medical profession today is described by Listner in U.S. Pat. No. 3,630,205.

As good as the current polypropylene sutures are, there is room for improvement. In particular, it would be desirable to increase the compliance, limpness, or felxibility of polypropylene sutures, especially with the larger suture sizes, in order to make them easier to handle and to improve their knot security. The problem is that previous efforts to accomplish this have occasioned a concomitant undesirable decrease in strength properties.

One approach to the provision of sutures having the desirable properties of polypropylene sutures, with the added feature of being more compliant, has been to employ random ethylene-propylene copolymers containing a small amount of polymerized ethylene, as is disclosed by Menezes et al. in U.S. patent application Ser. No. 432,487, filed Oct. 4, 1982, entitled "Ethylene-Propylene Copolymer Sutures", and assigned to the same assignee as this application, and abandoned Nov. 28, 1984.

The extrusion of polymers into monofilaments is well established technology, as is illustrated by the Listner patent cited above. The typical procedure is to extrude the monofilament and pass it to a first station such as a godet. The monofilament is quenched, either by air or by a liquid quench bath, between the extruder and the first station. The monofilament may be "drawn down" slightly between the extruder and the first station, but the draw down ratio or "jet stretch" (i.e., ratio of speed of take up at the first station to extrusion speed) will rarely exceed about 4X. After the first station, the monofilament is oriented by drawing. In order to achieve uniform orientation, the degree of draw achieved between the first station and the next station should be the "natural draw ratio". The natural draw ratio is defined as the ratio of take-up speed to let-off speed at which an undrawn filament will spontaneously draw via a "neck" formation when subjected to an axial extension above the filament's yield point. The natural draw ratio is a moderately narrow range of draw ratios that is dependent, in part, upon factors such as nature of polymer, molecular weight, drawing conditions, especially temperature, and the like. If the draw ratio used is less than the natural draw ratio, undrawn areas of monofilament will be present, and if the draw used in a single drawing step is above the natural draw ratio, microscopic inhomogeneities such as voids and fibrils will be formed.

This invention is directed to the provision of improved polypropylene surgical monofilaments that are significantly more compliant than prior polypropylene surgical monofilaments (as is evidenced by significantly lower Young's Modulus values), but which retain, at least to a large degree, the excellent properties of prior polypropylene surgical monofilaments, and to a method for producing the improved sutures. The process for producing the surgical monofilaments of this invention involves additional orientation in one or more added drawing stages beyond that achieved by the initial draw that is carried out at the natural draw ratio, followed by a heat relaxation step with annealing.

This invention is based upon the discovery that an increase in the draw ratio during orientation increases the tensile strength more than the modulus of the filament, and that an increase in the shrinkage allowed during annealing decreases the modulus more than the tensile strength. Thus, an increase in both the draw ratio and the allowed shrinkage during annealing results in a filament of lower modulus at a given level of tensile strength.

SUMMARY OF THE INVENTION

The improved, sterile polypropylene surgical monofilaments of the invention are characterized by an improved ratio of tensile strength to Young's modulus. For instance, by following the teachings of this invention it is possible to maintain the current level of tensile strength at reduced Young's modulus values, and, conversely, to maintain the same level of Young's modulus and increase the tensile strength.

The process of the invention comprises the steps of:

(a) extruding polypropylene through an orifice and quenching rapidly to produce a filament and passing said filament continuously from said orifice to a first station;

(b) drawing said filament from said first station to a second station under such conditions that said filament is drawn between said first and second stations at about its natural draw ratio;

(c) subjecting the filament to additional drawing of from about 1.06 to about 1.5X after said second station so that the filament is subjected to a total draw of from about 1.06 to about 1.5X the natural draw ratio;

(d) collecting the thus drawn filament; and (e) subjecting the collected filament to a heat relaxation step at elevated temperature of from, for example, about 135° C. to about 152° C., to effect a linear shrinkage in the filament of from about 16 to about 35 percent of the said collected filament, and heat setting this thus shrunken filament.

THE PRIOR ART

U.S. Pat. No. 3,630,205, to Listner, discloses polypropylene monofilament sutures produced by extruding isotactic polypropylene to form a monofilament, stretching the monofilament at elevated temperature to about 6.6 times its original length, and subsequently permitting the stretched monofilament to contract to between 91% and 76% of its stretched length.

U.S. Pat. No. 3,161,709, to Noether et al., discloses the production of isotactic polypropylene filaments wherein the polypropylene is extruded, is drawn from the extruder at a linear speed faster than the polypropylene leaves the extruder, and is then subjected to two additional drawing steps to achieve a total draw ratio of at least about 9:1 and preferably at least about 12:1.

Several other patents disclose the production of polypropylene filaments which are stretched after having been produced, and which may or may not be heat relaxed after the initial stretching. Such patents include Roberts et al., U.S. Pat. No. 3,048,467, Compostella et al., U.S. Pat. No. 3,106,442, Martin, U.S. Pat. No. 3,152,380, and Bierbaum et al., U.S. Pat. No. 3,413,397.

Northey, in U.S. Pat. No. 3,359,983, discloses surgical sutures made from polypropylene which is stretched to several times its original length after having been cast or extruded.

It is known as a general principle in the art that drawing unoriented fibers generally results in fibers of increased crystallinity and molecular orientation. Increased crystallinity and oritentation usually increase the tensile strength and elastic modulus, and decrease the break elongation. Thus, the general principle is that drawing results in stiffer fibers having greater straight tensile strengths, but, in many cases, reduced knot strength. It is also a known general principle that annealing with shrinkage of drawn fibers reduces the tensile strength and elastic modulus, thereby resulting in weaker but limper fibers.

BRIEF DESCRIPTION OF THE DRAWING

The FIGURE is a side elevation, partially schematic, of an apparatus suitable for carrying out the process of the invention.

DETAILED DESCRIPTION OF THE INVENTION

The preferred isotactic polypropylene for use in the invention is a fiber forming grade having a weight average molecular weight of above about 250,000. This material is readily available commercially in both powder and pellet form.

Referring to the FIGURE, there is shown an apparatus that is suitable for carrying out the extrusion and drawing steps of the process of the invention. An extruder 10 is terminated at one end with an extrusion die 12. A longitudinal extruder screw is mounted for rotation within a barrel 16 and is driven by a variable speed motor 18 through a gear 20. Polypropylene pellets are introduced into the extruder through a hopper 22 which communicates with the barrel 16. In normal operation of the extruder 10, the feeding zone 24 of the extruder is maintained at a temperatue of about 196° C., the transition zone 26 is maintained at a temperature between about 199° and about 227° C., and the pump block 30, die 12, and die block 28 are maintained at a temperature between about 199° and about 227° C. A pump 33 driven by a motor 32 pumps the molten polypropylene through spinneret orifices in the die 12 to form a plurality of filaments 31 (for simplification, shown as one filament in the FIGURE). The filament 31 is extruded into a quench bath 34 that is maintained at a convenient temperature, such as room temperature, below about 50° C., around an idler roll 36 in the quench bath 34, and then up out of the quench bath 34 to another idler roll 35 to the first godet 37. The surface of the liquid in the quench bath 34 is preferably not more than a few centimeters below the die 12, in order to achieve rapid quenching of the extruded filament 31. In the ordinary course of carrying out the process of the invention, the first godet 37 will be rotating at a peripheral speed that is up to about 4 times the speed that the monofilament 31 is extruded from the die orifice 12. At greater speeds, one observes the onset of "draw resonance", which is a pulsation resulting in periodic diameter changes.

A draw ratio higher than the natural draw ratio may be achieved in several ways. However, in general a higher temperature is necessary to avoid defects. Also, it is preferable to "ease" the monofilament into higher orientation levels by incrementally drawing the monofilaments in several stages. Consequently, in the preferred embodiment the filament 31 is first passed around the first godet 37, which includes a main roll 38 and an air bearing 40. The filament 31 then proceeds to the second godet 42 comprising a main roll 44 and an air bearing 46. The second godet 42 is rotating at a peripheral speed such that the filament 31 will be drawn at its natural draw ratio between the first godet 37 and the second 42. For the preferred polypropylene, this draw ratio will usually be between about 6.0 and 7.0X. After passing around the second godet 42, the filament 31 then proceeds to a third godet 48 comprising a main roll 50 and an air bearing 52. The third godet 48 is rotating at a peripheral speed of from about 1.02 to about 1.2 times the peripheral speed of the second godet 42.

After passing several times around the third godet 48, the filament 31 then passes through an oven 54 that is maintained at a temperature of from about 120° to about 150° C., to a fourth godet 56 including a main roll 58 and an air bearing 60, that are rotating at peripheral speeds of about 1.10 and 1.20 times the peripheral speed of the third godet 48. After passing several times around the fourth godet 56, the filament 31 then proceeds to a windup station 62.

The main roll 38 in the first godet 37 is ordinarily heated and is maintained at a temperature of from about 90° to about 110° C. Similarly, the main roll 44 in the secon godet 42 is normally maintained at an elevated temperature of from about 90° to about 110° C. The main roll 50 in the third godet 48 is ordinarily not heated, and will obtain an equilibrium temperature slightly above ambient temperature. The filament 31 is carried through the heated oven 54 so that it will attain a temperature of from about 80° to about 120° C. while in the oven. The fourth godet 56 is unheated.

The overall draw ratio, that is, the difference between the peripheral speed of the fourth godet 56 and the first godet 37, will ordinarily be from about 7.0X to about 10.0X, thereby achieving a total draw ratio of from about 1.06 to about 1.52X above the natural draw ratio.

After the filament 31 has been drawn in accordance with the procedures described above, it is then annealed in an oven and allowed to shrink from about 16 to about 35 percent of the original length (i.e., the final length will be from about 65 to 84 percent of the pre-shrink length). The annealing is carried out at a temperature within the range of from about 135° to about 152° C., for a period of time sufficient to permit the filament to shrink to the degree indicated above and heat set at that shrinkage. Normally, this will take from about 5 to about 40 minutes.

After the drawing the heat relaxation, the filaments of the invention are fabricated into surgical sutures in accordance with customary procedures. They can be produced in the usual sizes, for example, from size 2 down to size 11/0. They can be attached to needles by the usual procedures, and can then be sterilized (as by using ethylene oxide) and packaged in sterile packs ready for use.

The polypropylene that is employed to produce the sterile sutures of the invention can contain the usual stabilizers against heat, ultraviolet, and oxidative degradation. Such stabilizers include hindered phenols, tertiary amines, and the like. The polypropylene can also contain dyes, colorants, and lubricants.

The examples below illustrate the invention:

Examples 1-3 (Size 0 Sutures) and Controls 1 and 2 (Sizes 0 and 1 Sutures

Commercial isotactic polypropylene having a melt flow of 6.36 (by ASTM D-1238, Condition L) is used to produce surgical sutures by the following procedure:

Polypropylene pellets are introduced into the extruder through the hopper 22 which communicates with the barrel 16. In normal operation of the extruder, the barrel feed zone 24 of the extruder is maintained at a temperature of about 196° C. The metering pump 30 is maintained at a temperature of about 193° C., the block 28 and the die 12 are both maintained at a temperature of about 207° C. The polymer is extruded through a single orifice of diameter 0.07 inch, and is immediately quenched in water maintained at 24° C.

The extruded filament is oriented to an 8.8X draw ratio in three stages, as indicated in Table I, below. In a subsequent operation, the filament is annealed at 149° C. for 10 to 30 minutes, with an allowed shrinkage of 25 to 33 percent. Table III, below, displays the resulting physical properties after aging for at least one month.

As a control, a suture of the same size is manufactured by the process of Listner, U.S. Pat. No. 3,630,205, using the same polypropylene polymer. The resultant properties are listed as Control Example 1 in Table II. The extrusion, drawing, and annealing conditions for Control Example 1 are displayed in Table I.

As a second control, the Listner process is modified so as to permit unrestrained shrinkage during annealing. The production conditions are displayed in Table I and the properties are displayed in Table II, as Control Example 2. (This control example is not intended to illustrate the prior art, but rather a modification thereof.) As Control Example 2 demonstrates, if one attempts to improve the compliance of prior art polypropylene monofilament sutures solely by subjecting the monofilament to greater shrinkage during the annealing step, while this does improve the compliance, there is an accompanying undesirable drop in tensile and knot strengths. From this it is clear that the additional orientation during the drawing operation is crucial to obtaining low modulus without unacceptable loss in knot and tensile strengths.

Examples 4-5 and Controls 3-4 (Size 3/0 and 4/0 Sutures)

Polypropylene monofilaments are extruded as described in Examples 1-3 and detailed in Table I, below. These monofilaments are drawn to a total of 8.8X in three stages, and subsequently annealed at 155° C. for 30 minutes with 25 percent allowed shrinkage. Table II displays the resultant properties after aging for at least one month.

Control sutures are manufactured from the same polypropylene polymer by the Listner process. The resulting properties are displayed in Table II.

TABLE I

| | EXTRUSION | | | | DRAWINGS | | | | | ANNEALING | | |
|---|---|---|---|---|---|---|---|---|---|---|---|---|
| | Block/Die Temp. (°C.) | Die Dia/ # holes (in/_) | Barrel Pump Pr (psi) | Quench Water Temp (°C.) | I Godet Speed/Temp (fpm/°C.) | II Godet Speed/Temp (fpm/°C.) | III Godet Speed/Temp (fpm/°C.) | Heated Oven (in/°C.) | IV Godet Speed/Temp (fpm/°C.) | % Relax- ation | Anneal Temp (°C.) | Anneal Time (min) |
| Example 1 Size 0 | 207/207 | .070/1 | 1500/450 | 24 | 25/104 | 190/104 | 200/25 | 72/149 | 220/25 | 25 | 149 | 30 |
| Example 2 Size 0 | 207/207 | .070/1 | 1500/450 | 24 | 25/104 | 190/104 | 200/25 | 72/149 | 220/25 | 33 | 149 | 30 |
| Example 3 Size 0 Control | 207/207 | .070/1 | 1500/450 | 24 | 25/104 | 190/104 | 200/25 | 72/149 | 220/25 | 25 | 149 | 10 |
| Example 1 Size 0 | 204/193 | .054/4 | 2000/NA | 24 | 25/25 | — | — | 72/107 | 165/25 | 16 | 141 | 10 |
| Example 2 Size 1 | 210/199 | .064/3 | 2000/NA | 24 | 22.5/25 | — | — | 72/107 | 148.5/25 | 29 | 149 | 30 |
| Example 4 Size 3/0 | 204/204 | .034/8 | 900/1050 | 28 | 27/82 | 160/88 | 190/25 | 72/149 | 238/25 | 25 | 155 | 30 |
| Example 5 Size 4/0 | 204/204 | .034/8 | 1000/1000 | 28 | 27/93 | 160/93 | 190/25 | 72/149 | 238/25 | 25 | 155 | 30 |
| Example 3 Size 3/0 Control | 220/220 | .034/8 | 2000/NA | 24 | 35/25 | — | — | 72/107 | 231/25 | 16 | 143 | 10 |
| Example 4 Size 4/0 | 220/220 | .034/8 | 2000/NA | 24 | 39.5/25 | — | — | 72/107 | 260.5/25 | 16 | 149 | 10 |

TABLE II

| Property | Size 0 | | | | Size 1 | Size 3/0 | Size 4/0 | Size 3/0 | Size 4/0 |
| --- | --- | --- | --- | --- | --- | --- | --- | --- | --- |
| | Example 1 | Example 2 | Example 3 | Control 1 | Control 2 | Example 4 | Example 5 | Control 3 | Control 4 |
| Diameter, mils | 14.19 | 15.03 | 14.5 | 15.2 | 16.76 | 8.3 | 7.1 | 9.5 | 7.5 |
| Knot pull, lbs. | 7.40 | 7.36 | 7.30 | 7.9 | 8.3 | 2.8 | 2.3 | 3.8 | 2.4 |
| Knot Intrinsic, psi (Knot Strength) | 40,000 | 41,500 | 44,000 | 43,500 | 37,600 | 51,700 | 58,100 | 53,600 | 54,300 |
| Straight Pull, lbs | 7.50 | 8.80 | 7.70 | 11.7 | 9.2 | 3.6 | 2.8 | 5.1 | 3.4 |
| Straight Intrinsic, psi (Tensile Strength) | 50,000 | 50,000 | 47,000 | 64,500 | 41,700 | 66,500 | 69,800 | 71,900 | 76,900 |
| Break Elongation, % | 34 | 50 | 33 | 50 | 62 | 45 | 49 | 47 | 46 |
| Young's Modulus, psi | 227,000 | 219,000 | 300,000 | 474,000 | 233,000 | 340,500 | 339,900 | 505,000 | 533,800 |
| Tensile Strength(psi) / Young's Modulus(psi) | 0.22 | 0.23 | 0.16 | 0.14 | 0.18 | 0.20 | 0.21 | 0.14 | 0.14 |

The straight tensile, knot tensile, Break elongation and Young's Modulus values reported herein were determined by an Instron Tensile Tester using the following instrument settings:

| | Gauge Length | Chart Speed | Crosshead Speed |
| --- | --- | --- | --- |
| Tensile Strength | 1″ | 5″/min | 1″/min |
| Knot Strength | 2″ | 10″/min | 2″/min |
| Break Elongation | 1″ | 5″/min | 1″/min |
| Young's Modulus | 5″ | 20″/min | 5″/min |

Examples 6–9 and Control 5

By procedures similar to those described above in Examples 1–3, sizes 6/0 and 7/0 surgical filaments were made from the same commercial polypropylene. The extrusion, drawing, and annealing conditions are displayed in Table III, and representative properties are displayed in Table IV. Control 5 is illustrative of the preparation of a size 7/0 polypropylene surgical monofilament using the preferred conditions of the Listner patent.

TABLE III

| | EXTRUSION | | | | DRAWINGS | | | | | | | |
|---|---|---|---|---|---|---|---|---|---|---|---|---|
| | Block Die Temp. (°C.) | Die Dia/ # holes (in/_) | Barrel/ Pump Pr (psi) | Quench Water Temp (°C.) | I Godet Speed/ Temp (fpm/°C.) | II Godet Speed/ Temp (fpm/°C.) | III Godet Speed/ Temp (fpm/°C.) | Heated Oven (in/°C.) | IV Godet Speed/ Temp | % Relax-ation | Anneal Temp (°C.) | Anneal Time (min.) |
| Example 6 Size 6/0 | 221/221 | 20/2 | 1750/350 | 24 | 25/104 | 654/104 | 200/24 | 72/132 | 220/25 | 25 | 154 | 30 |
| Example 7 Size 6/0 | 221/221 | 20/2 | 1750/350 | 24 | 25/104 | 165/104 | 200/24 | 72/132 | 220/25 | 34 | 154 | 30 |
| Example 8 Size 7/0 | 221/221 | 20/2 | 1600/250 | 24 | 25/105 | 165/104 | 200/24 | 72/127 | 220/25 | 25 | 154 | 30 |
| Example 9 Size 7/0 | 221/221 | 20/2 | 1600/250 | 24 | 25/104 | 165/104 | 200/24 | 72/127 | 220/25 | 34 | 154 | 30 |
| Control 5 Size 7/0 | 221/232 | 20/1 | NA/NA | 24 | 50/25 | — | — | 84/140 | 330/25 | 16 | 140 | 10 |

TABLE IV

| Property | Size 6/0 | | Size 7/0 | | |
| --- | --- | --- | --- | --- | --- |
| | Example 6 | Example 7 | Example 8 | Example 9 | Control 5 |
| Diameter, mils | 3.29 | 3.76 | 2.43 | 2.97 | 2.60 |
| Knot pull, lbs | .46 | .45 | .28 | .30 | 0.54 |
| grams | — | — | 129 | 135 | 249 |
| Knot Intrinsic, psi (Knot Strength) | 54,000 | 41,000 | 61,436 | 43,000 | 90,300 |
| Straight Pull, lbs | .60 | .46 | .42 | .30 | 0.48 |
| grams | — | — | 191 | 137 | 221 |
| Straight Intrinsic, psi (Tensile Strength) | 71,000 | 42,000 | 91,000 | 44,000 | 101,600 |
| Break Elongation, % | 50 | 118 | 48 | 84 | 41 |
| Young's Modulus, psi | 270,000 | 251,000 | 358,000 | 221,000 | 449,000 |
| Tensile Strength(psi) / Young's Modulus(psi) | 0.26 | 0.17 | 0.25 | 0.20 | 0.23 |

As the foregoing Examples and Controls illustrate, when the process of the invention is carried out under optimum conditions, polypropylene monofilaments not heretofore available are produced. Over the full range of U.S.P. suture sizes, that is, from size 11/0 to size 2, the novel monofilaments have a combination of tensile strength (above 45,000 psi), knot strength (above 38,000 psi), break elongation (30 to 75%), Young's modulus (below 400,000 psi and preferably below 300,000 psi), and ratio of tensile strength to Young's modulus (above 0.20 and preferably above 0.21), not exhibited by prior art polypropylene monofilaments. While some prior art polypropylene monofilaments will have some or even a majority of these properties (for instance, the monofilament of Control 8 has four of the five properties), as far as the inventors herein are aware, no prior art teaching or technology can provide polypropylene monofilaments that have all five of these properties over the full range of suture sizes.

It is a characteristic of polypropylene monofilament sutures (both the prior art and this invention) that there is an inverse relationship between monofilament diameter and both intrinsic tensile strength and Young's modulus. Thus, the larger size sutures tend to have lower intrinsic tensile strength and Young's modulus values than do the smaller size sutures when produced by the same drawing and annealing processes. For factors that are apparently related to this reason, the process of this invention provides polypropylene monofilament sutures in the mid- to large size range (i.e., U.S.P. size 2 to 4/0) that are novel, even though they have tensile strength to Young's modulus ratios below 0.20. These novel size 2 to 4/0 polypropylene sutures have intrinsic tensile strengths above 45,000 psi, knot strengths above 38,000 psi, elongations above 30 percent (and preferably below 100 percent), and tensile strength to Young's modulus ratios (in psi) of at least 0.17, preferably above 0.18, and more preferably above 0.19. Preferably, these size 2 to 4/0 sutures have Young's modulus values below 500,000 psi, and more preferably, below 400,000 psi.

A major contribution of the process of the invention is that it enables the provision of polypropylene monofilaments that have increased compliance (as exhibited by reduced Young's modulus) without having a concommitant undesirable degree of loss in tensile strength. Thus, in the definition of the novel monofilaments that can be produced by the process of the invention, this contribution is embodied in the requirements of having a minimum tensile strength, a maximum Young's modulus, and a minimum ratio of tensile strength to Young's modulus. All three of these requirements are important in this respect.

What is claimed is:

1. An isotactic polypropylene surgical monofilament of size 11/0 to size 2, said polypropylene monofilament having the following properties:

| | |
| --- | --- |
| Tensile Strength | Above 45,000 psi |
| Knot Strength | Above 38,000 psi |
| Break Elongation | 30 to 75% |
| Young's Modulus | Below about 400,000 psi |
| Ratio of Tensile Strength (in psi) to Young's Modulus (in psi) | At least 0.20 |

2. A sterile needled suture wherein the suture comprises the monofilament of claim 1.

3. The isotactic polypropylene surgical monofilament of size 11/0 to size 2 to claim 1, said polypropylene monofilament having the following properties:

| | |
| --- | --- |
| Tensile Strength | Above 50,000 psi |
| Knot Strength | Above 40,000 psi |
| Break Elongation | 30 to 75% |
| Young's Modulus | Below about 300,000 psi |
| Ratio of Tensile Strength (in psi) to Young's Modulus (in psi) | Above 0.21 |

4. A sterile needled suture wherein the suture comprises the monofilament of claim 3.

5. An isotactic polypropylene surgical monofilament of size 4/0 to size 2, said polypropylene monofilament having the following properties:

| | |
| --- | --- |
| Tensile Strength | Above 45,000 psi |
| Knot Strength | Above 38,000 psi |
| Elongation | Above 30 percent |
| Ratio of Tensile Strength (in psi) to Young's Modulus (in psi) | At least 0.18 |

6. A sterile needled suture wherein the suture comprises the monofilament of claim 5.

7. The polypropylene monofilament of claim 5 wherein said monofilament has an elongation below 100 percent, a Young's modulus below 500,000 psi, and a tensile strength to Young's modulus ratio above 0.18.

8. A sterile needled suture wherein the suture comprises the monofilament of claim 7.

9. The polypropylene monofilament of claim 7 wherein said monofilament has a Young's modulus below 400,000 psi and a tensile strength to Young's modulus ratio above 0.19.

10. A sterile needled suture wherein the suture comprises the monofilament of claim 9.

* * * * *